US009931166B2

(12) United States Patent
Sauro et al.

(10) Patent No.: US 9,931,166 B2
(45) Date of Patent: *Apr. 3, 2018

(54) OFFSET CATHETER

(71) Applicant: The Spectranetics Corporation, Colorado Springs, CO (US)

(72) Inventors: Dennis M. Sauro, Glenmoore, PA (US); William T. Fisher, Schwenksville, PA (US)

(73) Assignee: The Spectranetics Corporation, Colorado Springs, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/230,148

(22) Filed: Aug. 5, 2016

(65) Prior Publication Data

US 2016/0338775 A1 Nov. 24, 2016

Related U.S. Application Data

(63) Continuation of application No. 12/333,427, filed on Dec. 12, 2008, now Pat. No. 9,408,665.

(51) Int. Cl.
| | |
|---|---|
| *A61B 18/20* | (2006.01) |
| *A61B 18/24* | (2006.01) |
| *A61M 25/00* | (2006.01) |
| *A61B 17/3207* | (2006.01) |
| *A61M 25/09* | (2006.01) |
| *A61B 18/22* | (2006.01) |

(52) U.S. Cl.
CPC .... *A61B 18/245* (2013.01); *A61B 17/320758* (2013.01); *A61B 18/24* (2013.01); *A61M 25/0068* (2013.01); *A61M 25/0074* (2013.01); *A61M 25/09* (2013.01); *A61B 2017/320775* (2013.01); *A61B 2018/2238* (2013.01); *A61B 2217/005* (2013.01); *A61M 25/007* (2013.01); *A61M 2025/09166* (2013.01)

(58) Field of Classification Search
CPC ............................ A61B 17/00; A61B 2017/00
See application file for complete search history.

(56) References Cited

U.S. PATENT DOCUMENTS 5,571,087 A * 11/1996 Ressemann ....... A61M 25/0068
604/264
2008/0097499 A1* 4/2008 Nash .............. A61B 17/320758
606/159

FOREIGN PATENT DOCUMENTS

JP 3144710 U * 9/2008

OTHER PUBLICATIONS

English Abstract of JP 3144710.*

* cited by examiner

*Primary Examiner* — Lynsey Eiseman
(74) *Attorney, Agent, or Firm* — Faegre Baker Daniels LLP

(57) ABSTRACT

Various embodiments of an offset catheter are provided. In some embodiments, an offset catheter includes a guidewire tube and a catheter coupled with an elastic and/or compressible rib. The compressible rib provides an offset or separation between the catheter and the guidewire tube in its resting state. The rib has an initial resting state, but may be forced into a compressed state. When released from the compressed state, the rib returns to its resting state. An offset catheter may be compressed and slid through a sheath. When the offset catheter emerges from the sheath, the distal tip will return to its resting state providing an operation offset.

15 Claims, 10 Drawing Sheets

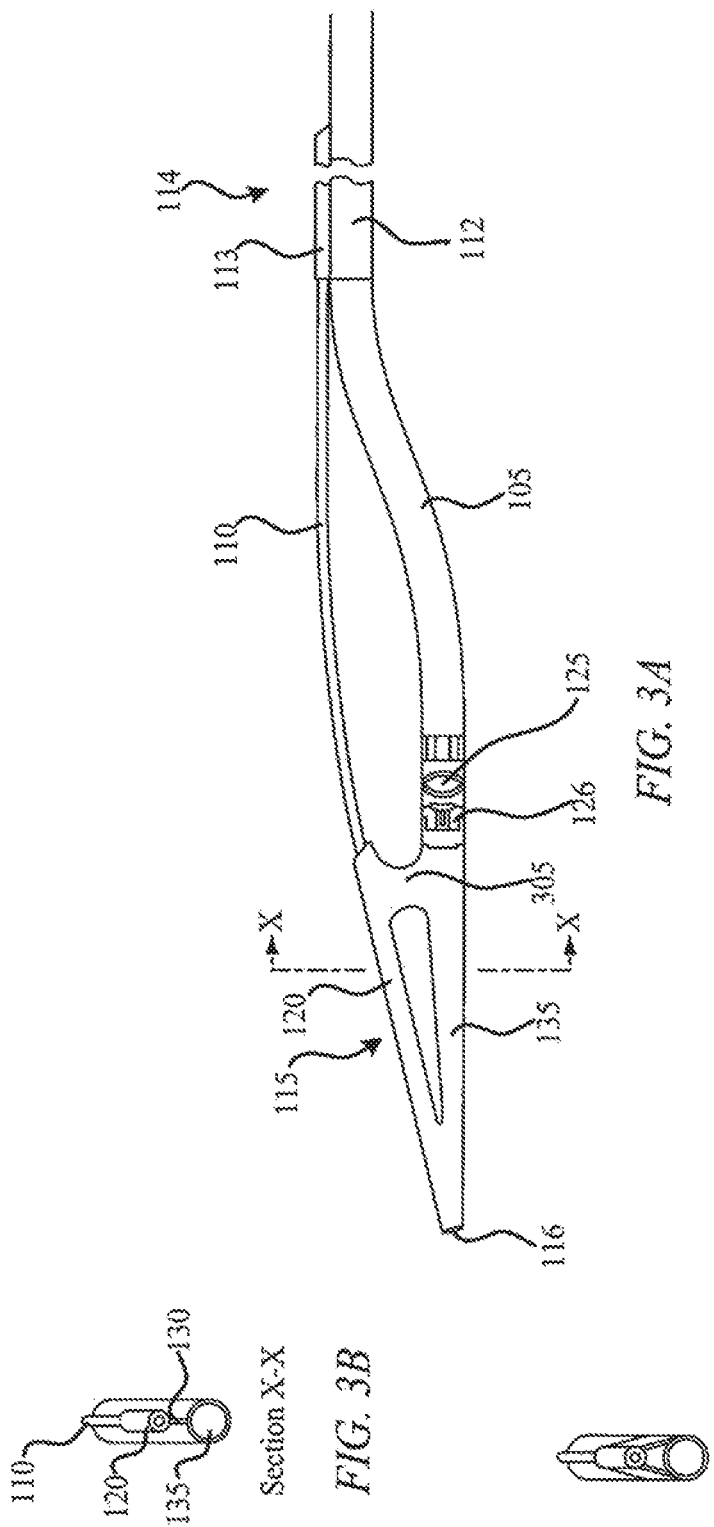

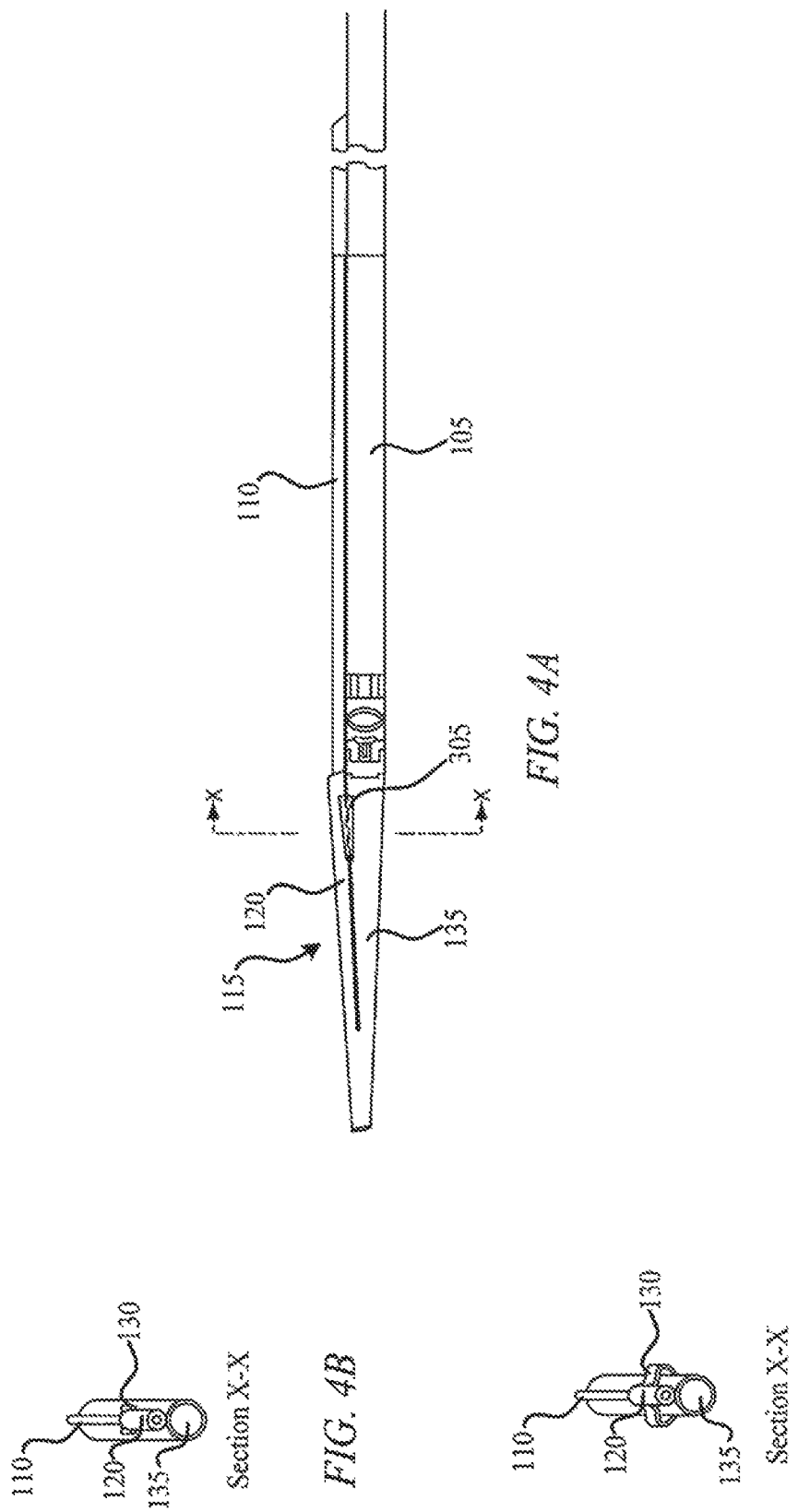

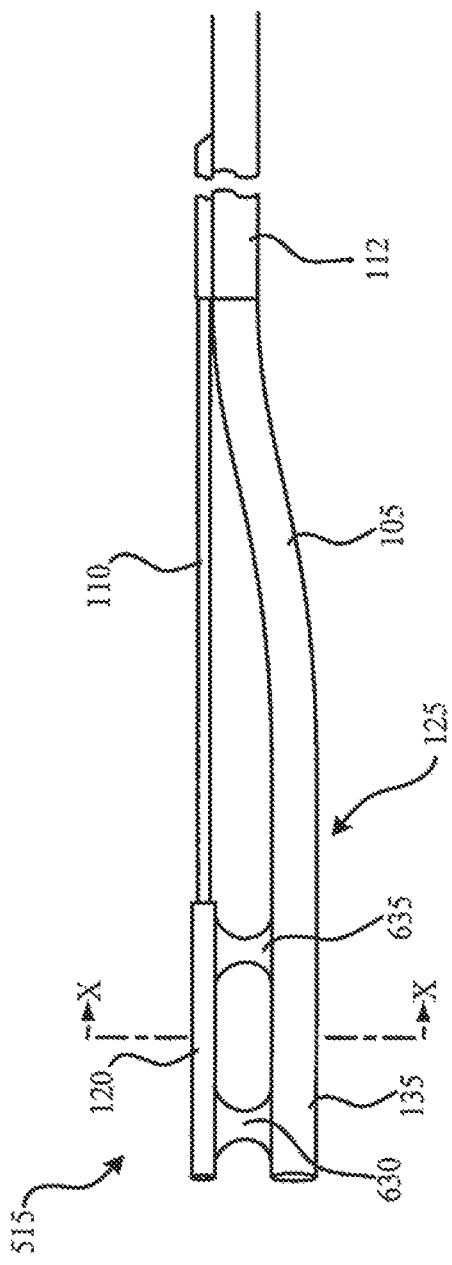
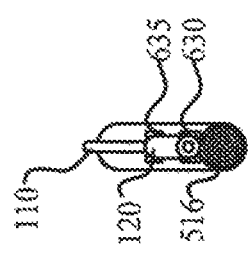
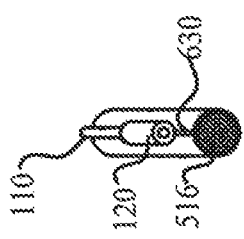
FIG. 6A
FIG. 6B
FIG. 6C

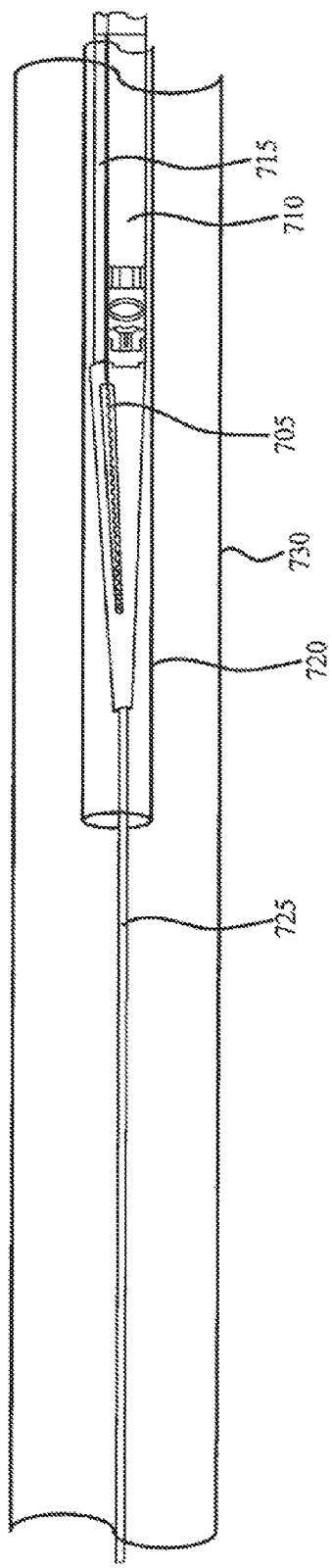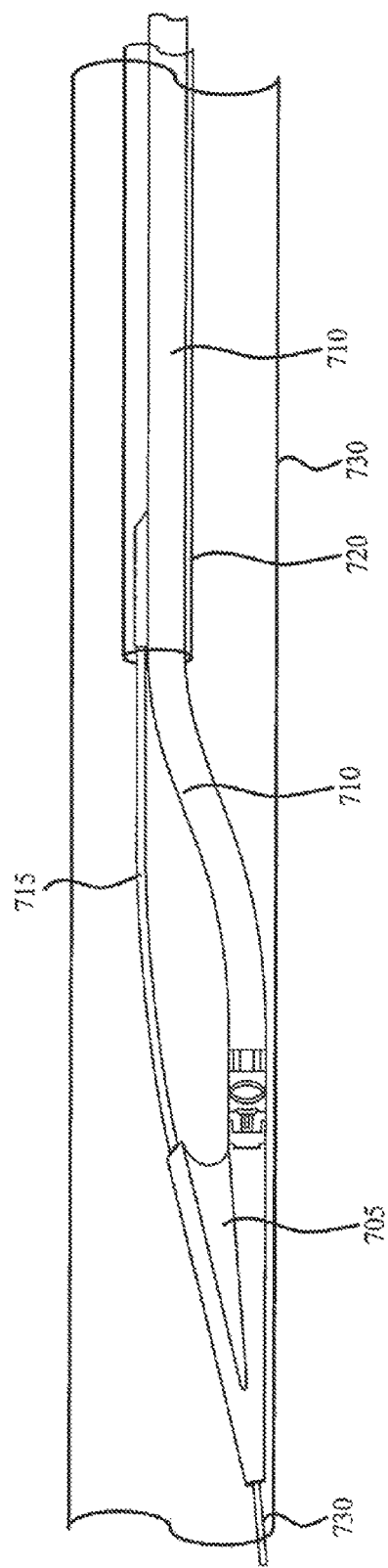

OFFSET CATHETER

CROSS REFERENCE TO RELATED APPLICATION

The present application is a divisional of prior U.S. application Ser. No. 12/333,427 filed Dec. 12, 2008, now U.S. Pat. No. 9,408,665, entitled OFFSET CATHETER, and incorporated herein by reference in its entirety, for all that it teaches and for all purposes.

BACKGROUND

This disclosure relates in general to catheters and, but not by way of limitation, to catheters with distal tips that are axially biased from a guidewire tube among other things.

Arteries are the primary blood vessels that are responsible for providing blood and oxygen to the heart muscle. Arterial disease occurs when arteries become narrowed or blocked by a buildup of plaque (as some examples, atherosclerotic plaque or other deposits). When the blockage is severe, the flow of blood and oxygen to the heart muscle is reduced, causing chest pain. Arterial blockage by clots formed in a human body may be relieved in a number of traditional ways. Drug therapy, including nitrates, beta-blockers, and peripheral vasodilatator drugs to dilate the arteries or thrombolytic drugs to dissolve the clot, can be effective. If drug treatment fails, angioplasty may be used to reform or remove the atherosclerotic plaque or other deposits in the artery.

Traditional balloon angioplasty is sometimes used to address the blockage by inserting a narrow, flexible lumen having a balloon into an artery in the arm or leg. The blocked area in the artery can be stretched apart by passing the balloon to the desired treatment site and gently inflating it a certain degree. In the event drug therapy is ineffective or angioplasty is too risky (often introduction of a balloon in an occluded artery can cause portions of the atherosclerotic material to become dislodged which may cause a total blockage at a point downstream of the subject occlusion thereby requiring emergency procedures), the procedure known as excimer laser angioplasty may be indicated.

Laser angioplasty procedure is similar in some respects to conventional coronary balloon angioplasty. A narrow, flexible lumen, the laser catheter, is inserted into an artery in the arm or leg. The laser catheter contains one or more optical fibers, which can transmit laser energy. The laser catheter is then advanced inside the artery to the targeted obstruction at the desired treatment site. After the laser catheter has been positioned, the laser is energized to "remove" the obstruction.

In many procedures, the lesion is often engaged similar to conventional balloon angioplasty by crossing the blockage with a guidewire. The laser catheter's thin, flexible optical fibers facilitate the desired positioning and alignment of the catheter. Using the excimer laser, the clinician performs a controlled blockage removal by sending bursts of ultraviolet light through the catheter and against the blockage, a process called "ablation." The catheter is then slowly advanced through the blockage reopening the artery. If there are multiple blockages, the catheter is advanced to the next blockage site and the above step is repeated. When the indicated blockages appear to be cleared, the catheter is withdrawn.

Mechanical thrombectomy catheters may be used to restore patency to a vessel that had been at least partially occluded by material. For example, rotary catheters may employ a rotary cutting head, a rotating macerator or some homogenization device to remove blockage by the effects of a hydrodynamic vortex generated near the blockage. Alternatively, some instruments repeatedly drum into the occlusive material, displacing and distorting the material in order to create a lumen there through, while leaving the material within the vessel. Arguably, for the long term benefit of the patient, it is desirable to effectuate the removal of the occlusive material, yet care must be taken to ensure that loose debris, such as fragments of thrombus, are unable to travel away from the site to cause a life threatening injury such as an embolism, stroke or heart attack.

Various devices have been devised to clear occlusive material resulting from laser and/or mechanical catheters in large vessels. Moreover, various biasing techniques have been employed to ablate blockages with dimensions larger than the catheter diameter. Yet, a need remains to provide catheters that aspirate and ablate within vessels with dimensions larger than catheter dimensions.

BRIEF SUMMARY

An offset catheter is provided according to various embodiments that comprises a catheter body, a guidewire tubular member configured to accept a guide wire, a working tubular member, and an elastic rib. The guidewire tubular member and the working tubular member are movable relative to each other near the distal end, and may be coupled with the elastic rib. The elastic rib may include a relaxed state that provides a separation between the working tubular member and the guidewire tubular member and/or a compressed state where the guidewire tubular member and the working tubular member are generally adjacent to each other. In some embodiments, the elastic rib comprises a thermoplastic elastomer.

An offset catheter is also provide that includes a guidewire tube, a catheter and separation means. The guidewire tube having a distal end and a proximal end. The catheter having a distal end and a proximal end. The separation means provides separation between the distal end of the catheter and the guidewire tube. The separation means may also be coupled with the catheter proximal to the distal end of the catheter and coupled with the guidewire tube proximal to the distal end of the guidewire tube.

An offset catheter distal tip is provided including a catheter coupler, a guidewire lumen, and an elastic member. The catheter coupler configured to couple with the distal and of a catheter. The elastic member may include a guide wire lumen, in some embodiments. In some embodiments, the guidewire lumen is coupled with the catheter coupler. The elastic member may also be configured to laterally separate the guide wire lumen from the catheter coupler in a relaxed state; and the elastic member being configured to collapse under mechanical pressure bringing the guidewire tube and the catheter coupler proximate to one another in a collapsed state.

Another offset catheter is provided comprising a guidewire tubular member, a laser catheter, a laser and an elastic rib. The guidewire tubular member including an inner lumen configured to accept a guide wire, a proximal end, and a distal end. The laser catheter including a proximal end coupled with the laser, and a distal end. The elastic rib may be coupled with the guidewire tube proximate to the distal end of the guidewire tube and coupled with the laser catheter proximate to the distal end of the laser catheter. The elastic rib may include a relaxed state that provides a separation between the distal end of the laser catheter and the guidewire tube.

In some embodiments, an offset catheter may include a second rib coupled with the guidewire tube proximate to the distal end of the guidewire tube and coupled with the working tubular member proximate to the distal end of the working tubular member. The working tubular member may include a light guide, an aspiration aperture, an aspiration macerator and/or an aspiration vacuum. The guidewire tube, for example, may comprises a stiffness that may be greater than the stiffness of a guidewire or a typical guidewire known in the art. The offset catheter may also include a proximal sheath that contains a portion of the catheter and a portion of the guidewire tube A method for using an offset catheter is also provided. A guidewire may be fed through at least a distal portion of the guidewire tube. In some embodiments, the guidewire is first introduced within a guidewire lumen in an elastic member or within a distal end. The guidewire having been previously positioned in some embodiments. The guidewire tube and the catheter may be pinched together forcing the distal tip and or the elastic rib into a collapsed state. The pinched together guidewire tube and catheter may then be slid through a catheter sheath. The guidewire tube, the catheter, the elastic rib and/or the distal tip may return to their relaxed state upon exit from the catheter sheath.

Further areas of applicability of the present disclosure will become apparent from the detailed description provided hereinafter. It should be understood that the detailed description and specific examples, while indicating various embodiments, are intended for purposes of illustration only and do not limit the scope of the disclosure.

BRIEF DESCRIPTION OF THE DRAWINGS

FIG. 3A is a side view of an offset catheter in a relaxed state according to one embodiment.

FIG. 3B is an end view of an offset catheter with a single rib in a relaxed state according to one embodiment.

FIG. 3C is an end view of an offset catheter with a double rib in a relaxed state according to one embodiment.

FIG. 4A is a side view of an offset catheter in a compressed state according to one embodiment.

FIG. 4B is an end view of an offset catheter with a single rib in a compressed state according to one embodiment.

FIG. 4C is an and view of an offset catheter with a double rib in a compressed state according to one embodiment.

FIG. 6A is a side view of an offset catheter in a relaxed state according to one embodiment.

FIG. 6B is an end view of an offset catheter with a roughly rectangular shaped double rib in a relaxed state according to one embodiment.

FIG. 6C is an end view of an offset catheter with a roughly rectangular shaped double rib in a compressed state according to one embodiment.

FIGS. 7A and 7B show an offset catheter being introduced into a vessel and the offset catheter positioned within the vessel according to one embodiment.

In the appended figures, similar components and/or features may have the same reference label. Where the reference label is used in the specification, the description is applicable to any one of the similar components having the same reference label.

DETAILED DESCRIPTION

The ensuing description provides various embodiments of the invention only, and is not intended to limit the scope, applicability or configuration of the disclosure. Rather, the ensuing description of the embodiments will provide those skilled in the art with an enabling description for implementing an embodiment. It should be understood that various changes may be made in the function and arrangement of elements without departing from the spirit and scope as set forth in the appended claims.

Embodiments of an offset catheter are provided throughout the specification. In one embodiment, an offset catheter is provided that includes a guidewire tube with an inner lumen and a catheter separated by an elastic and collapsible rib in a relaxed state. In some embodiments, the catheter may provide aspiration of occlusive material. Such catheters are provided in U.S. patent application Ser. No. 10/832,830, U.S. patent application Ser. No. 11/751,443, and U.S. patent application Ser. No. 11/871,908 each of which are entitled "Thrombectomy and Soft Debris Removal Device" and each of which are incorporated herein for all purposes. The catheter, in other embodiments, may be a laser catheter. The rib may encompass a portion of the catheter and/or a portion of the guidewire tube. In one embodiment, the rib may be triangularly shaped when the rib is in a relaxed (not compressed) state. For example, the guidewire tube may extend along a first triangular edge of the rib and may have an exit aperture, for example, at the apex of the triangle. The catheter may extend along a second triangular edge and may meet at the apex of the triangle. In other embodiments, a stiffening member may extend along the second triangular edge instead of the catheter. The stiffening member, for example, may be coupled with the distal tip of the stiffening member.

In use, the offset catheter may be collapsed and slid through the sheath of a catheter. For example, the collapsible rib may be collapsed by pinching the guidewire tube together with the catheter or stiffening member. When the collapsible rib has been collapsed the guidewire tube and the catheter or stiffening member are contiguous and/or somewhat parallel with one another. The catheter may then be slid through a sheath. When the catheter exits the sheath the collapsible rib may elastically expand separating the distal end of the catheter and the guidewire tube. In some embodiments, such an arrangement may allow an aspiration catheter to aspirate debris within a large vessel that is axially distant from the guidewire tube. In other embodiments, such an arrangement may also allow a laser catheter to ablate axially distant blockage within a large vessel.

Figure 1A:
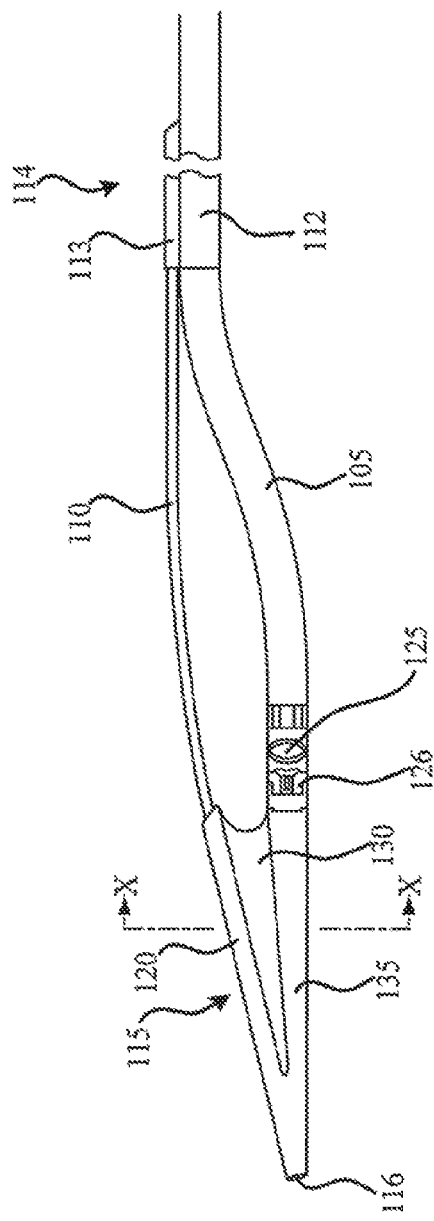
FIG. 1A is a side view of an offset catheter with a full rib in a relaxed state according to one embodiment.
Figure 1B:
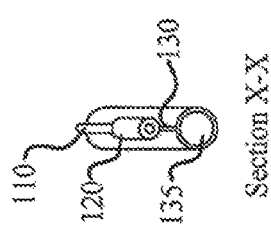
FIG. 1B is an end view of an offset catheter in a relaxed state according to one embodiment.
Figure 2A:
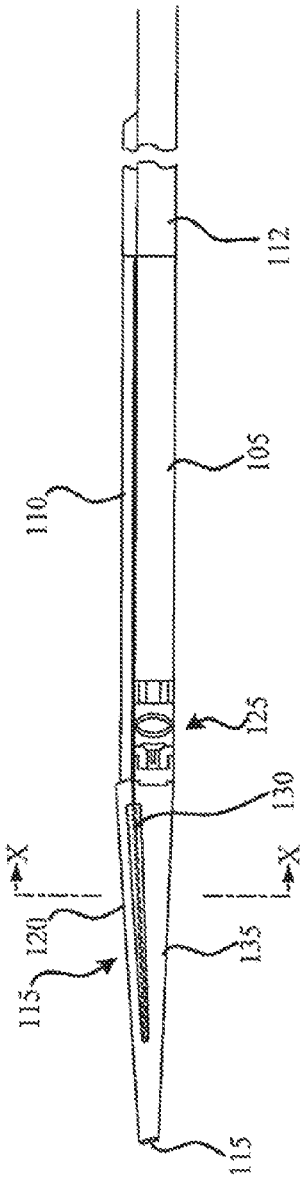
FIG. 2A is a side view of an offset catheter with a full rib in a compressed state according to one embodiment.

FIG. 1A shows a side view of an offset catheter with a full rib 130 in a relaxed state according to one embodiment. FIG. 1B shows an end view of the offset catheter in FIG. 1A along line X-X. The offset catheter includes guidewire tube 110, catheter 105, and a distal tip 115. Distal tip 115 includes an elastic and/or collapsible rib 130 that, in some embodiments, extends triangularly between distal tip guidewire lumen 120 and distal tip support member 135 (or stiffening member). Rib 130 may comprise a thermoplastic elastomer (TPE). In other embodiments, rib 130 may include various polymer and non-polymer materials. In some embodiments, rib 130 may also comprise a material that can be stretched or collapsed under stress and, upon the removal of stress, rib 130 will return to substantially close to its original shape. Rib 130 may be collapsed under stress and/or external forces as shown in FIG. 2A. When the stress and/or external forces are released, rib 130 may return to its relaxed state as shown in FIG. 1A. Rib 130, in some embodiments, may include a spring or any other elastic material that is also compressible.

Distal tip guidewire lumen 120 may include guidewire exit aperture 116. Thus, a guidewire may be introduced into the catheter through guidewire exit aperture 116. The guidewire may then slide through distal tip guidewire lumen 120 and guidewire tube 110. In some embodiments, guidewire tube 110 may extend through catheter body 114 and/or extend through a sheath. In some embodiments, a proximal guidewire lumen 113 may also be utilized. Guidewire tube 110 may comprise a material, such as, for example, polyimide, polyketone, and/or polyetheretherketone (PEEK). In some embodiments, guidewire tube 110 may be carbon fiber reinforced. In some embodiments, guidewire tube 110 may comprise a material with stiffness greater than a guidewire used with the offset catheter and/or greater than the stiffness of a typical guidewire. Moreover, guidewire tube 110, in some embodiments, may be manufactured with an elastic material in a curved shaped, for example, as shown in FIG. 1A. Thus, when distal tip guidewire lumen 120 and guidewire tube 110 are released from being restrained in a straight configuration, guidewire tube 110 may return to its curved shape. Distal tip guidewire lumen 120 may include a radio opaque marker band (not shown) near guidewire exit aperture 116. In some embodiments, distal tip 115, including distal tip guidewire lumen 120 and distal tip support member 135, may comprise a single molded material. In yet another embodiment, distal tip 115 may include a catheter coupler that couples the distal tip 115 with catheter 105.

Catheter 105 may include an aspiration catheter, a laser catheter and/or a mechanical catheter. FIG. 1A shows an aspiration catheter that includes one or more aspiration apertures 125. Aspiration apertures 125 may be disposed within the distal end of catheter 105 and/or within the circumference or periphery of catheter 105. Catheter 105 may also include a macerating head or a cutting head 126 at the distal end of catheter 105. The macerating head or a cutting head 126, for example, may include a helical head. Catheter 105 may comprise an aspiration catheter, for example, as described in U.S. patent application Ser. No. 10/832,830, U.S. patent application Ser. No. 11/751,443, and U.S. patent application Ser. No. 11/871,908 each of which are entitled "Thrombectomy and Soft Debris Removal Device." Catheter 105 may include a tubular member or a tube with an inner lumen.

Distal tip 115 provides lateral separation between guidewire tube 110 and the distal end of catheter 105 in the distal tip's 115 relaxed state. In some embodiments, distal end of catheter 105 may include a radio opaque marker band. Moreover, catheter 105, in some embodiments, may be manufactured with an elastic material in a curved shaped, for example, as shown in FIG. 1A. Thus, when catheter 105 is released from being restrained in a straight configuration, catheter 105 returns to its curved shape.

Catheter 105 may include a catheter tubular member, a tube, or a sheath with an inner lumen. In some embodiments, catheter 105 may comprise a laser catheter. In such embodiments, catheter 105 may include one more optical fibers that extend from the proximal end of catheter 105 toward the distal end of catheter 105 within the inner lumen. A laser coupler may be coupled with the catheter at the proximal end of catheter 105. The laser coupler may be coupled with a laser. In some embodiments, catheter 105 may include a liquid light guide. In other embodiments, catheter 105 may include both a liquid light guide and one or more optical fibers.

Figure 2B:
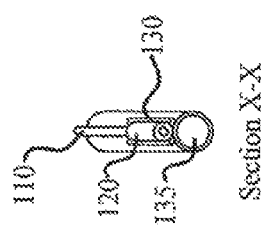
FIG. 2B is an end view of an offset catheter in a compressed state according to one embodiment.

FIG. 2A shows a side view of an offset catheter with a full rib 130 in a compressed state according to one embodiment. FIG. 2B shows the end view of the offset catheter in FIG. 2A along line X-X. As shown, distal tip 115 is compressed by forcibly compressing and/or pinching distal tip guidewire lumen 120 and distal tip support member 135 together. In the compressed state, rib 130 is folded or bunched together as shown in FIG. 2B. Moreover, in the compressed state, the offset catheter may slidably fit within a sheath. Thus, in use, an offset catheter may be compressed (for example, as shown in FIG. 2A), placed within the proximal end of a sheath, and then slid through the sheath. Alternatively, distal tip 115 may be introduced into sheath or any other lumen, and due to its triangular shape the rib may collapse allowing the offset catheter to slide within the sheath. When the offset catheter emerges from the distal end of the sheath, the distal tip may return to its relaxed shape as shown in FIG. 1A.

A secondary sheath may also be employed in some embodiments. A secondary sheath may slide relative to the offset catheter and may be used to collapse the offset catheter. The secondary sheath may be used to collapse the collapsible rib during introduction of the catheter into lumen or sheath. The secondary sheath may also be used when the offset catheter is located within a vessel to collapse the offset catheter in order to move the offset catheter through a narrower stenosis or a portion of the vessel with a smaller inner diameter. Accordingly, the user may be able to move the secondary sheath relative to the offset catheter to collapse the offset catheter when in use.

FIG. 3A is a side view of an offset catheter in a relaxed state according to another embodiment. FIG. 3B shows the end view of the offset catheter in FIG. 3A along line X-X with a single rib. FIG. 3C shows the end view of the offset catheter in FIG. 3A along line X-X with a double rib. As shown in FIG. 3A, in this embodiment, rib 305 is not triangular shaped as shown in FIG. 1A; and rib 305 is not in full contact with distal tip guidewire lumen 120 and/or distal tip support member 135 as shown in FIG. 1A. In some embodiments, rib 305 may be a single rib (as shown in FIG. 3B) or may be a double rib (as shown in FIG. 3C). As shown in FIG. 3C, a double rib may be coupled with the periphery of the distal tip guidewire lumen 120 and distal tip support member 135.

FIG. 4A shows a side view of an offset catheter with a partial rib in a compressed state. FIG. 4B shows an end view of the compressed offset catheter in FIG. 4A with a single rib and FIG. 4C shows an end view of the compressed offset catheter in FIG. 4A with a double rib. As shown in FIG. 4C, one or two ribs may be coupled with the side of either or both of distal tip guidewire lumen 120 and/or distal tip support member 135.

Figure 5A:
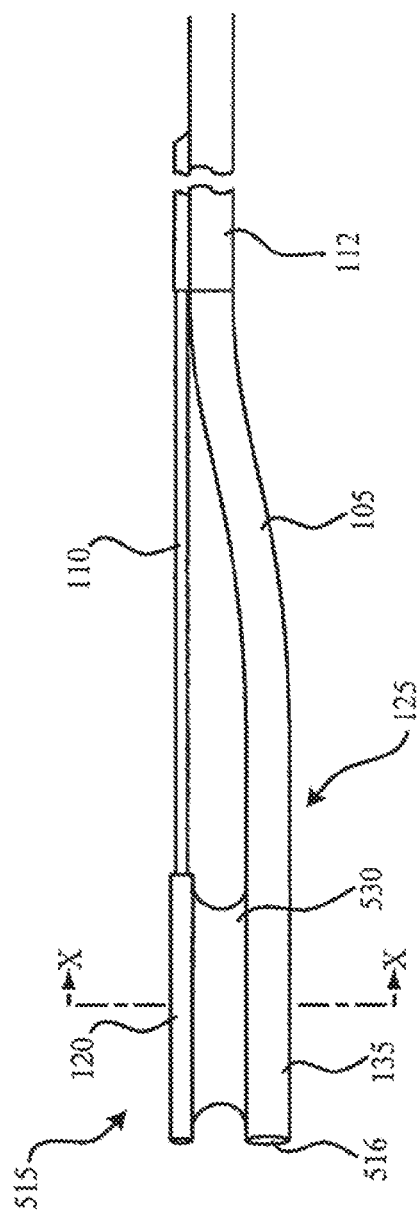
FIG. 5A is a side view of an offset catheter in a relaxed state according to one embodiment.
Figure 5B:
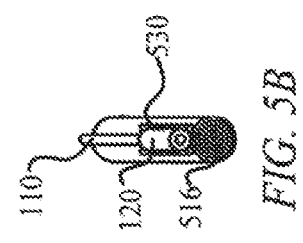
FIG. 5B is an end view of an offset catheter with a roughly rectangular shaped rib in a relaxed state according to one embodiment.
Figure 5C:
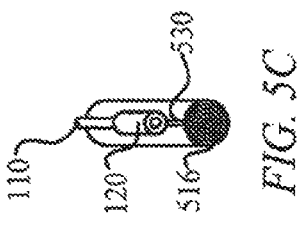
FIG. 5C is an end view of an offset catheter with a roughly rectangular shaped rib in a compressed state according to one embodiment.

FIG. SA shows a side view of an offset catheter with a full rectangular rib 530 in a relaxed state according to one embodiment. FIG. 5B shows an end view of the offset catheter in FIG. 5A along line X-X in a relaxed state and FIG. 5C shows another end view of the offset catheter in FIG. 5A along line X-X in a compressed state. As shown, rib 530 may be roughly rectangular shaped. Moreover, distal tip 515 does not include a distal tip support member. Rather, rib 530 is coupled with distal tip guidewire lumen 520 and catheter 505. Accordingly, rib 530 provides separation between the distal end of distal tip guidewire lumen 520 and the distal end of catheter 505. Moreover, rib 530 may also keep distal tip guidewire lumen 520 and the distal end of catheter 505 parallel to one another. Catheter 505 may include a laser catheter comprising, for example, a fiber optic bundle that extends to distal end 516. Catheter 135 as shown in FIGS. 5B and 56 comprises a laser catheter with a plurality of optical fibers 516.

Rib 530 may comprise a thermoplastic elastomer (TPE). In other embodiments, rib 530 may include various polymer and non-polymer materials. In some embodiments, rib 530 may also comprise a material that can be stretched or collapsed under stress and, upon the removal of stress, return to substantially close to its original shape. Rib 530 may be collapsed under stress and/or external forces. When the stress and/or external forces are released, rib 530 may return to its relaxed state.

FIGS. 6A, 6B and 6C show various views of an offset catheter similar to the offset catheter shown in FIGS. SA, 5B and 5C, but with two ribs 630 and 635. Rib 630 is located near the distal ends of distal tip guidewire lumen 120 and distal tip support member 135.

FIG. 7A shows an offset catheter with a collapsed elastic rib 705 disposed between a guidewire lumen in a distal tip or a guidewire tube 715 and a distal tip support member. The offset catheter is shown within a lumen of a sheath or elongated body 720. As shown, catheter 710 and guidewire tube are roughly proximate with each other within the sheath 720. Sheath 720 may be advanced within vessel 730 with the offset catheter inside. The sheath may follow guidewire 725. Once in position, the offset catheter may be advanced from within sheath 720 as shown in FIG. 7B. Once elastic rib 705 has exited sheath 720, rib 705 returns to its relaxed state. In the relaxed state, the distal end of catheter 710 and guidewire 715 are separated by rib 705. The offset affected by rib 705 in the relaxed state may provide some force against the material to be removed. For example, a rotary aspiration catheter may increase performance when the catheter is pressed against the material being removed. The offset may provide positive tool pressure against the material being removed thereby maintaining engagement with the material being removed and increasing the effectiveness of the aspiration. In such a state, the offset catheter may be advanced within vessel 730. Moreover, offset catheter may be reintroduced within sheath 720 by sliding the offset catheter backwards into sheath 720. In doing so, the offset catheter returns to it collapsed state.

Figure 8:
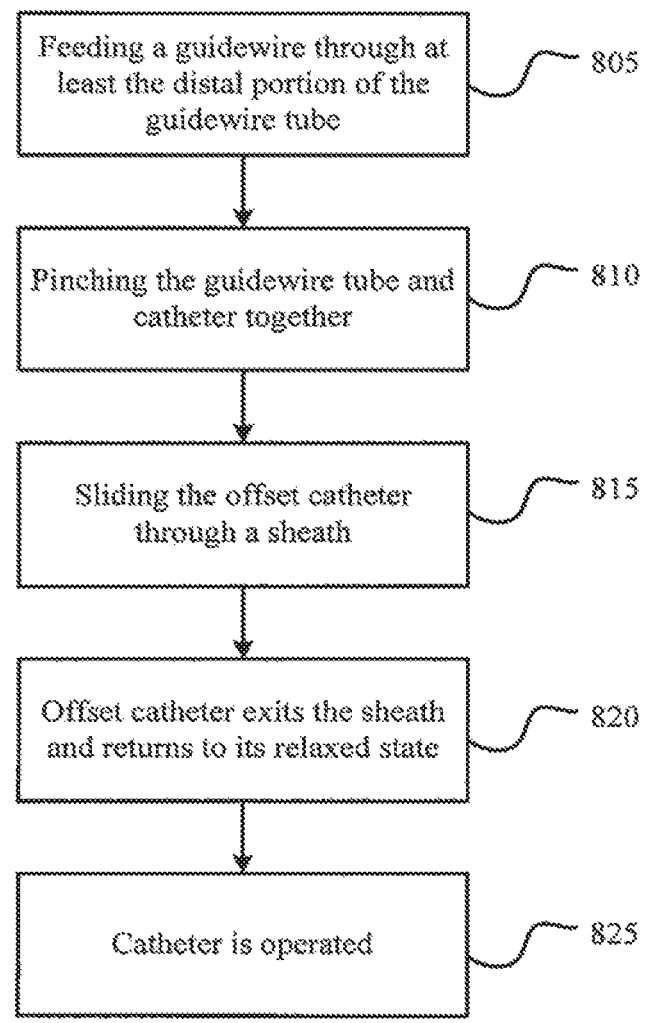
FIG. 8 shows a flowchart describing the use of an offset catheter according to one embodiment.

FIG. 8 shows describes a method of operating an offset catheter according to another embodiment. A guidewire is fed through the guidewire tube at block 805. In some embodiments, the guidewire may first be fed through the guidewire lumen of an elastic distal tip. In some embodiments, guidewire may also be fed into the guidewire tube while the offset catheter is housed within or without a sheath. The guidewire tube and the catheter are placed in a collapsed state by pinching the two together at block 810. In doing so, a rib between the two may be elastically collapsed. The offset catheter may then be slid through a sheath at block 815. The offset catheter may then exit the proximal end of the sheath, whereupon the offset catheter and/or distal tip return to a relaxed state at block 820. Elastic material in the distal tip, the rib, the catheter, and/or the guidewire tube may provide the requisite force to return the offset catheter to its relaxed state. The catheter may then be operated at block 825. In some embodiments, a laser catheter is activated. In other embodiments, an aspiration catheter is used. The offset catheter may be advanced independent and/or with the sheath as needed.

In order to treat an area and/or volume the offset catheter may be rotated about the offset catheter's central axis. Alternatively, distal tip may be rotated about the catheter guidewire tube's central axis. For example, the user may apply a torque at the proximal end of the working catheter that causes the distal tip to rotate axially.

Figure 9:
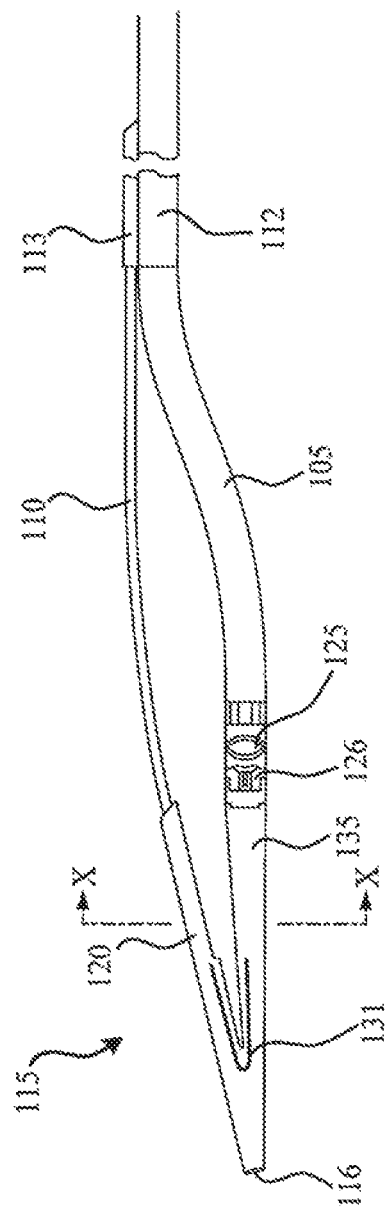
FIG. 9 is a side view of an offset catheter in a relaxed state according to one embodiment.

FIG. 9 shows another offset catheter providing separation between the distal end of a working catheter 105 and guidewire lumen 120 and/or guidewire tube 110 in a relaxed state according to another embodiment. In this embodiment, a spring member 131 coupled with guidewire lumen 120 of distal tip 115 and/or distal tip support member 135. In some embodiments, spring member 131 is coupled with working catheter 105 and/or guidewire tube 110. In some embodiments, spring member 131 may be comprised of flat or round wire. In some embodiments, spring member 131 may be embedded within distal tip 115. The spring member 131 may have a higher melting point than distal tip 115 so that spring member 131 may be insert molded into distal tip 115. Spring member 131 may bias guidewire lumen 120 of distal tip 115 and distal tip support member 135 by exerting a separation force.

Figure 10:
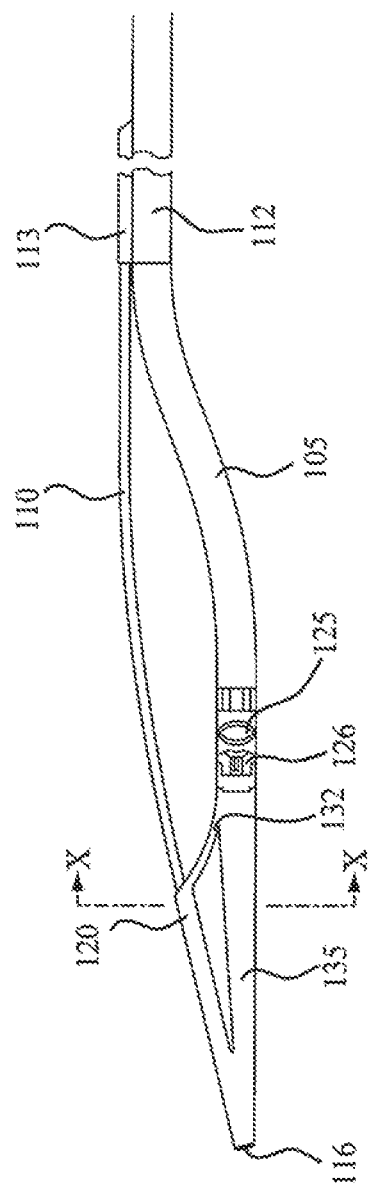
FIG. 10 is a side view of another offset catheter in a relaxed state according to one embodiment.

FIG. 10 shows another configuration of an offset catheter according to another embodiment. In this embodiment rib 132 is oriented in the relaxed state such that when collapsed, rib 132 lays flat proximate with distal tip support member 135.

While the principles of the disclosure have been described above in connection with specific apparatuses and methods this description is made only by way of example and not as limitation on the scope of the disclosure.

What is claimed is:

1. A catheter system comprising:
  a catheter having a proximal end and a distal end;
  a tip coupled to the distal end of the catheter, wherein the tip comprises a first edge, a second edge, a longitudinal axis between the first edge and the second edge, and a guidewire lumen adjacent the first edge, wherein the guidewire lumen is configured to be coupled to a guide wire, the tip comprising an elastic member coupled with the catheter along the second edge, the elastic member configured to laterally separate the guide wire lumen from the catheter in a relaxed state, and the elastic member configured to collapse from the first edge to the second edge under mechanical pressure, thereby bringing the guidewire lumen and the catheter proximate to one another in a collapsed state in which the elastic member is at least partially folded along the longitudinal axis.

2. The catheter system according to claim 1, wherein the tip comprises molded plastic.

3. The catheter system according to claim 1, further comprising a radio opaque marker band at a proximal end of the guidewire lumen.

4. The catheter system according to claim 1 wherein the catheter comprises one or more light guides.

5. The catheter system according to claim 4 wherein the catheter comprises an aspiration aperture.

6. The catheter system according to claim 5 wherein the catheter comprises an aspiration lumen coupled with the aspiration aperture.

7. The catheter system according to claim 1 wherein the catheter comprises a cutting head or a macerating head.

8. The catheter system according to claim 7 wherein the catheter comprises an aspiration aperture.

9. The catheter system according to claim 8 wherein the catheter comprises an aspiration lumen coupled with the aspiration aperture.

10. The catheter system according to claim 1, wherein the elastic member comprises a triangular shape.

11. The catheter system according to claim 10, wherein the elastic member comprises a triangular shape in the relaxed state.

12. The catheter system according to claim 1, wherein the elastic member comprises a rectangular shape.

13. The catheter system according to claim 12, wherein the elastic member comprises a rectangular shape in the relaxed state.

14. The catheter system according to claim 1, wherein the elastic member comprises a curved shape.

15. The catheter system according to claim 14, wherein the elastic member comprises a curved shape in the relaxed state.

\* \* \* \* \*